United States Patent [19]
Snow et al.

[11] Patent Number: 5,932,188
[45] Date of Patent: Aug. 3, 1999

[54] THERAPEUTIC AND DIAGNOSTIC IMAGING COMPOSITIONS AND METHODS

[75] Inventors: Robert A. Snow, West Chester; David L. Ladd, Wayne; John L. Toner, Downingtown, all of Pa.

[73] Assignee: Sterling Winthrop Inc., New York, N.Y.

[21] Appl. No.: 08/963,125

[22] Filed: Oct. 28, 1997

Related U.S. Application Data

[63] Continuation of application No. 08/493,523, Jun. 22, 1995, abandoned, which is a continuation of application No. 08/352,682, Nov. 30, 1994, abandoned, which is a continuation of application No. 07/960,745, Oct. 14, 1992, abandoned.

[51] Int. Cl.$^6$ .......................... A61K 51/04; A61B 5/055; C07F 5/00
[52] U.S. Cl. .................. 424/1.65; 424/1.69; 424/9.36; 424/9.3; 424/9.361; 534/10; 534/14
[58] Field of Search .................. 424/1.65, 1.69, 424/9.36, 9.361, 9.3; 534/10, 14

[56] References Cited

U.S. PATENT DOCUMENTS

| | | | |
|---|---|---|---|
| 3,859,337 | 1/1975 | Herz et al. | 562/512 X |
| 4,407,978 | 10/1983 | Kahovec et al. | 521/56 |
| 4,423,158 | 12/1983 | Porath | 521/32 |
| 4,556,689 | 12/1985 | Murakami et al. | 525/54.1 |
| 4,602,097 | 7/1986 | Curtis | 549/27 |
| 4,615,879 | 10/1986 | Runge et al. | 424/9 |
| 4,647,447 | 3/1987 | Gries et al. | 424/9 |
| 4,687,658 | 8/1987 | Quay | 424/9 |
| 4,687,659 | 8/1987 | Quay | 424/9 |
| 4,746,507 | 5/1988 | Quay | 424/9 |
| 4,804,529 | 2/1989 | Bardy et al. | 424/9 |
| 4,814,098 | 3/1989 | Inada et al. | 252/62.51 |
| 4,822,594 | 4/1989 | Gibby | 424/9 |
| 4,826,673 | 5/1989 | Dean et al. | 424/9 |
| 4,859,451 | 8/1989 | Quay et al. | 424/9 |
| 4,909,257 | 3/1990 | Engelstad et al. | 128/654 |
| 4,916,246 | 4/1990 | Felder et al. | 556/1 |
| 4,933,441 | 6/1990 | Gibby | 536/112 |
| 4,943,523 | 7/1990 | Stavrianopoulos | 435/7 |
| 4,963,344 | 10/1990 | Gries et al. | 424/9 |
| 4,972,837 | 11/1990 | Engelstad et al. | 562/444 |
| 4,980,148 | 12/1990 | Dean | 424/9 |
| 4,980,502 | 12/1990 | Felder et al. | 424/9 |
| 4,985,233 | 1/1991 | Klaveness et al. | 424/9 |
| 4,986,980 | 1/1991 | Jacobsen | 424/9 |
| 5,057,302 | 10/1991 | Johnson et al. | 424/1.1 |
| 5,077,037 | 12/1991 | Wallace | 424/9 |
| 5,141,966 | 8/1992 | Porath | 521/32 |
| 5,281,704 | 1/1994 | Love et al. | 540/465 |
| 5,283,339 | 2/1994 | Arnold et al. | 548/104 |
| 5,385,719 | 1/1995 | Unger et al. | 528/272 |

FOREIGN PATENT DOCUMENTS

| | | |
|---|---|---|
| 0200467 | 11/1986 | European Pat. Off. . |
| 0277 088A2 | 8/1988 | European Pat. Off. . |
| 0430863 | 6/1991 | European Pat. Off. . |
| 0450742 | 10/1991 | European Pat. Off. . |
| 0466200 | 1/1992 | European Pat. Off. . |
| 0481 526A1 | 4/1992 | European Pat. Off. . |
| WO 94/01393 | 1/1994 | Japan . |
| 9004384 | 10/1988 | WIPO . |
| 9001024 | 2/1990 | WIPO . |
| 9012050 | 10/1990 | WIPO ........................ A61K 49/02 |
| 9115753 | 10/1991 | WIPO . |
| 9118630 | 12/1991 | WIPO . |
| WO 91/18630 | 12/1991 | WIPO . |
| WO 93/06148 | 4/1993 | WIPO . |

OTHER PUBLICATIONS

International search report dated Apr. 8, 1994, PCT/US93/09645.
Radiolabeling of New Polymer Chelates (PC) M. Chinol et al., Poster Sessions, vol. No. 31, dated May 1990.
Yokoyama et al, "Molecular Design for Missile Drug . . . " Makromol. Chem. 190,2041–2054 (1989) without month.
Schuhmann–Giampieri et al, "In Vivo and In Vitro Evaluation of Gd–DTPA–Polylysine . . . " Investigative Radiology, 969–974, (1991) without month.
Marchal et al, "MR Angiography with Gadopentetate . . . " AJR:155, 407–411 (1990) without month.
Mutter, "Soluble Polymers in Organic Synthesis:I. Preparation of Polymer Reagents . . . " Tetrahedron Letters, 31,2839–42 (1978).
Harris et al, Synthesis & Characterization of Poly(Ethylene Glycol) Derivatives. J. of Poly. Science, 22, 341–352 (1984).
Shen et al, "Copolymeric MR Contrast Agents", J. Mag. Res. IM., 2, 115 (1992).

*Primary Examiner*—Jose' G. Dees
*Assistant Examiner*—Michael G. Hartley
*Attorney, Agent, or Firm*—Fish & Richardson P.C.

[57] ABSTRACT

This invention provides therapeutic and diagnostic imaging compositions and methods featuring a polymer comprising units containing a poly(alkylene oxide) moiety linked to the residue of a chelating agent, said polymer having a cytotoxic agent associated therewith.

15 Claims, No Drawings

THERAPEUTIC AND DIAGNOSTIC IMAGING COMPOSITIONS AND METHODS

CROSS REFERENCE TO RELATED APPLICATIONS

This is a continuation of application Ser. No. 08/493,523, filed Jun. 22, 1995, now abandoned, which is a continuation of application Ser. No. 08/352,682, filed Nov. 30, 1994, now abandoned, which is a continuation of application Ser. No. 07/960,745, filed Oct. 14, 1992, now abandoned.

Reference is hereby made to commonly assigned copending U.S. patent applicaton Ser. No. 07/961,146, filed Oct. 14, 1992, now abandoned, entitled CHELATING POLYMERS and U.S. patent application Ser. No. 07/960,745, filed Oct. 14, 1992, entitled MR IMAGING COMPOSITIONS AND METHODS filed concurrently herewith.

FIELD OF INVENTION

The present invention relates to targeting polymers useful in therapeutic and diagnostic imaging compositions and methods.

BACKGROUND OF THE INVENTION

The concept of drug targeting has gained importance in recent years, especially for anticancer drugs, inasmuch as toxic side effects of anticancer drugs to normal cells are a primary obstacle in cancer chemotherapy due to lack of selectivity to cancer cells. Drug targeting can be accomplished by conjugation with, or encapsulation in a specific transporter to the target. Materials such as proteins, saccharides, lipids and synthetic polymers have been used for such transporters. Antibodies have been perhaps most widely used due to their target specificity and wide applicability.

Yokohama et al, Makromol. Chem. 190, 2041–2054 (1989) describe adriamycin conjugated with immunoglobulin G using polytethylene glycol)-block-poly(aspartic acid) as a carrier. The adriamycin is bound to the poly(aspartic acid) chain and immunoglobulin G is attached to the poly (aspartic acid) via disulfide linkages.

Recently, substances substituted with PEG chains for treating or diagnosing tumors have been described in PCT/EP91/00992. However, there is no suggestion of a polymer containing units comprising a poly(alkylene oxide) moiety linked to a chelating agent.

It is apparent that it would be desirable to provide new classes of materials having a specificity toward accumulation in different tissues, and which remain in the blood pool for long periods of time.

SUMMARY OF THE INVENTION

We have discovered that reactive poly(alkylene oxides) can be contacted with chelating agents or precursors thereof containing reactive functionality to form targeting polymers which, when associated with cytoxic agents, find particular utility in therapeutic and diagnostic imaging compositions and methods.

More particularly, in accordance with this invention, there is provided a polymer comprising units containing a poly (alkylene oxide) moiety linked to the residue of a chelating agent, said polymer having a cytotoxic agent or residue of a cytotoxic agent associated therewith.

This invention further provides a pharmaceutical composition comprising the above-described polymer and a method for treating disease sites in a patient comprising administering to the patient an effective amount of the above-described polymer.

It is an advantageous feature of this invention that polymeric compounds are provided having a specificity toward accumulation in different tissues, for example, in tumors and the liver.

It is another advantageous feature of this invention that a wide variety of polymers of specified compositions, size and molecular weight can be prepared in accordance with this invention.

Still another advantageous feature of this invention is that polymeric compounds are provided which remain in the blood pool within the vasculature for remarkably long periods of time.

Other advantageous features of this invention will become readily apparent upon reference to the following description of the preferred embodiments.

DESCRIPTION OF PREFERRED EMBODIMENTS

While this invention is described herein primarily in connection with polymers containing units comprising a poly(alkylene oxide) moiety, it is believed to be useful in conjunction with polymers comprising units containing other biocompatible polymers.

The polymer of this invention comprises units containing the residue of a chelating agent linked to a poly(alkylene oxide) moiety in the backbone of the polymer. The polymer can comprise from 2 to 1000 or more, preferably 3 to 1000 of the above-described units. In preferred embodiments, the above-described units are recurring units.

The polymer of this invention has a cytotoxic agent or the residue of a cytotoxic agent associated therewith. By "cytotoxic agent", it is meant any agent able to kill cells, including radionuclides, toxins, and chemotherapeutic agents such as cytoxic drugs and cytotoxic antibiotics, or any agent that initiates or activates a host's immune response which leads to cell death. The cytotoxic agent can be ionically associated with the residue of the chelating agent. For example, in preferred embodiments, the cytotoxic agent is a radionuclide comprising a radioactive metal ion such as described below associated with the residue of the chelating agent. Alternatively, the cytotoxic agent can be covalently bonded to the residue of the chelating agent or to the linking group. In such cases, the residue of the cytotoxic agent is that portion of the cytotoxic agent that is attached to or subtended from the covalent bond to the residue of the chelating agent or linking group. As used herein, the term "cytotoxic agent" is intended to include residues of cytotoxic agents which are covalently bonded to the polymer at one or more sites of attachment, the inherent cytotoxic properties of the agent being maintained or regenerated as a result of cleavage of said bond or bonds.

In preferred embodiments, the above-described polymer comprises units having the structure I:

I.

$$-[(Z)^{(d)}-L-(Q)-L_1]-$$
$$\quad\quad\quad |$$
$$\quad\quad [M^{(+a)}]_r$$
$$\quad\quad [E^{(b)}]_w$$

wherein:

Z is the residue of a chelating agent;

Q is a poly(alkylene oxide) moiety;

L and $L_1$ independently represent a chemical bond or a linking group;

$M^{(+a)}$ is one or more radioactive metal ions having a total charge of +a;

$E^{(b)}$ is one or more counterions having a total charge of b;

w is 0 or 1;

r is 0 or 1;

d is the total charge on the linked residue of the chelating group; and a=d+b.

In formula I above, Q represents a linear or branched poly(alkylene oxide) moiety. Exemplary poly(alkylene oxide) moieties include poly(ethylene oxides), poly (propylene oxides) and poly(butylene oxides). Preferred poly(alkylene oxides) include poly(ethylene oxides) (PEO), poly(propylene oxides) (PPO) and random and block copolymers of PEO and PPO. PEO containing polymers are particularly preferred when it is desired for the final polymer to possess solubility in water. It is also contemplated that the poly(alkylene oxide) moiety can comprise glycerol poly (alkylene oxide) triethers, polyglycidols, and linear, block and graft copolymers of alkyleneoxides with compatible comonomers such as poly(ethyleneimine-co-ethylene oxide) and poly(methyl vinyl ether-co-ethylene oxide). The poly (alkylene oxide) moieties have a molecular weight from 100–200,000, preferably 250–100,000 and more preferably 250–20,000 daltons. Preferred moieties can be derived from poly(alkylene oxide) moieties which are commercially available in the corresponding diol form and/or can be prepared by techniques well known to those skilled in the art. A particularly preferred class of PEO moieties derived from PEGs can be represented by the structure —$(CH_2CH_2O)_mCH_2CH_2$— wherein m is 1 to 5,000, preferably 1 to 2500, and more preferably 1 to 500.

The polymer of the invention can comprise the residue of one or more of a wide variety of chelating agents. As is well known, a chelating agent is a compound containing donor atoms that can combine by coordinate bonding with a cation to form a cyclic structure called a chelation complex or chelate. This class of compounds is described in the Kirk-Othmer Encyclopedia of Chemical Technology, Vol. 5, 339–368.

The residues of suitable chelating agents can be derived from and selected to contain chelating elements selected from polyphosphates, such as sodium tripolyphosphate and hexametaphosphoric acid;

aminocarboxylic acids, such as ethylenediaminetetraacetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentacetic acid;

1,3-diketones, such as acetylacetone, trifluoroacetylacetone, and thenoyltrifluoroacetone;

hydroxycarboxylic acids, such as tartaric acid, citric acid, gluconic acid, and 5-sulfosalicylic acid;

polyamines, such as ethylenediamine, diethylenetriamine, triethylenetetramine, and triaminotriethylamine;

aminoalcohols, such as triethanolamine and N-(2-hydroxyethyl)ethylenediamine;

aromatic heterocyclic bases, such as 2,2'-dipyridyl, 2,2'-diimidazole, dipicoline amine and 1,10-phenanthroline;

phenols, such as salicylaldehyde, disulfopyrocatechol, and chromotropic acid;

aminophenols, such as 8-hydroxyquinoline and oxinesulfonic acid;

oximes, such as dimethylglyoxime and salicylaldoxime;

peptides containing proximal chelating functionality such as polycysteine, polyhistidine, polyaspartic acid, polyglutamic acid, or combinations of such amino acids;

Schiff bases, such as disalicylaldehyde 1,2-propylenediimine;

tetrapyrroles, such as tetraphenylporphin and phthalocyanine;

sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea;

synthetic macrocylic compounds, such as dibenzo[18] crown-6, $(CH_3)_6$-[14]-4,11-diene-$N_4$, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred residues of chelating agents contain polycarboxylic acid or carboxylate groups and include elements present in: ethylenediamine-N,N,N',N'-tetraacetic acid (EDTA); N,N,N',N'',N''-diethylenetriaminepentaacetic acid (DTPA); 1,4,7,10-tetraazacyclododecane-N,N',N'',N'''-tetraacetic acid (DOTA); 1,4,7,10-tetraazacyclododecane-N, N',N''-triacetic acid (DO3A); 1-oxa-4,7,10-triazacyclododecane-N,N',N''-triacetic acid (OTTA); trans (1,2)-cyclohexanodiethylenetriamine pentaacetic acid (CDTPA);

(B4A)

(P4A)

(TMT)

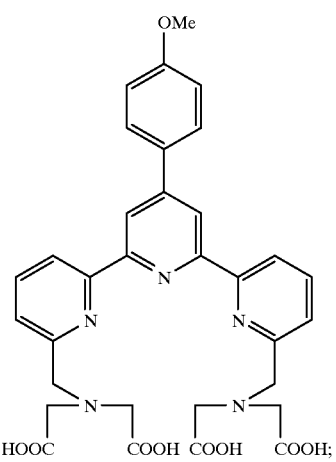

(DCDTPA)

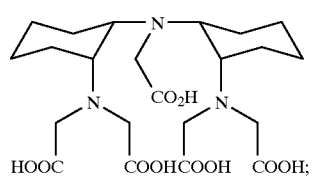

and (PheMT)

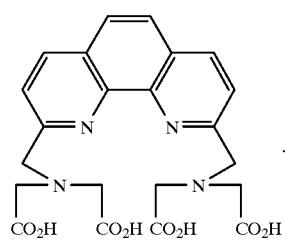

Other suitable residues of chelating agents are described in PCT/US91/08253, the disclosure of which is hereby incorporated by reference. In formula I above, Z is the residue of one or more chelating agents. If Z is the residue of multiple chelating agents, such agents can be linked together by a linking group such as described below.

The residue of the chelating agent is linked to the poly (alkylene oxide) moiety through a chemical bond or a linking group, i.e., L and $L_1$ in formula I above. Preferred linking groups include nitrogen atoms in groups such as amino, imido, nitrilo and imino groups; alkylene, preferably containing from 1 to 18 carbon atoms such as methylene, ethylene, propylene, butylene and hexylene, such alkylene optionally being interrupted by 1 or more heteroatoms such as oxygen, nitrogen and sulfur or heteroatom-containing groups;
carbonyl;
sulfonyl;
sulfinyl;
ether;
thioether;
ester, i.e., carbonyloxy and oxycarbonyl;
thioester, i.e., carbonylthio, thiocarbonyl, thiocarbonyloxy and oxythiocarbonyl;
amide, i.e., iminocarbonyl and carbonylimino;
thioamide, i.e., iminothiocarbonyl and thiocarbonylimino;
thio;
dithio;
phosphate;
phosphonate;
urelene;
thiourelene;
urethane, i.e., iminocarbonyloxy and oxycarbonylimino;
thiourethane, i.e., iminothiocarbonyloxy, and oxythiocarbonylimino;
an amino acid linkage, i.e., a

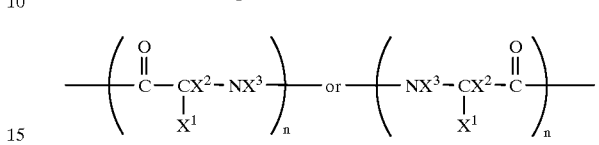

group wherein n=1 and $X^1$, $X^2$ and $X^3$ independently are H, alkyl, containing from 1 to 18, preferably 1 to 6 carbon atoms, such as methyl, ethyl and propyl, such alkyl optionally being interrupted by 1 or more heteroatoms such as oxygen, nitrogen and sulfur, substituted or unsubstituted aryl, containing from 6 to 18, preferably 6 to 10 carbon atoms such as phenyl, hydroxyiodophenyl, hydroxyphenyl, fluorophenyl and naphthyl, aralkyl, preferably containing from 7 to 12 carbon atoms, such as benzyl, heterocyclyl, preferably containing from 5 to 7 nuclear carbon and one or more heteroatoms such as S, N, P or O, examples of preferred heterocyclyl groups being pyridyl, quinolyl, imidazolyl and thienyl; heterocyclylalkyl, the heterocyclyl and alkyl portions of which preferably are described above; or a peptide linkage, i.e., a

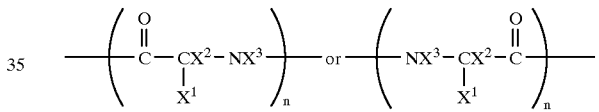

group wherein n>1 and each $X^1$, $X^2$ and $X^3$ are independently represented by a group as described for $X^1$, $X^2$ and $X^3$ above. Two or more linking groups can be used, such as, for example, alkyleneimino and iminoalkylene. It is contemplated that other linking groups may be suitable for use herein, such as linking groups commonly used in protein heterobifunctional and homobifunctional conjugation and crosslinking chemistry. Especially preferred linking groups include unsubstituted or substituted imino groups which when linked to the carbonyl in the residue of a chelating agent forms an amide group.

The linking groups can contain various substituents which do not interfere with the polymerization reaction. The linking groups can also contain substituents which can otherwise interfere with the polymerization reaction, but which during the polymerization reaction, are prevented from so doing with suitable protecting groups commonly known in the art and which substituents are regenerated after the polymerization by suitable deprotection. The linking groups can also contain substituents that are introduced after the polymerization. For example, the linking group can be substituted with substituents such as halogen, such as F, Cl, Br or I; an ester group; an amide group; alkyl, preferably containing from 1 to about 18, more preferably, 1 to 4 carbon atoms such as methyl, ethyl, propyl, i-propyl, butyl, and the like; substituted or unsubstituted aryl, preferably containing from 6 to about 20, more preferably 6 to 10 carbon atoms such as phenyl, naphthyl, hydroxyphenyl, iodophenyl, hydroxyiodophenyl, fluorophenyl and methoxyphenyl; substituted or unsubstituted aralkyl, preferably containing from 7 to about 12 carbon atoms, such as benzyl and phenylethyl; alkoxy, the alkyl portion of which preferably contains from 1 to 18 carbon atoms as described for alkyl above; alkoxyaralkyl, such as ethoxybenzyl; substituted or unsubstituted heterocyclyl, preferably containing from 5 to 7 nuclear carbon and heteroatoms such as S, N, P or O, examples of preferred heterocyclyl groups being pyridyl, quinolyl, imidazolyl and thienyl; a carboxyl group; a carboxyalkyl group, the alkyl portion of which preferably contains from 1 to 8 carbon atoms; the residue of a chelating group, preferably comprised of elements such as described for Z above but being subtended from the backbone at one covalent site of such elements; or a poly(alkylene oxide) moiety, preferably such as described for Q above but being subtended from the backbone of the polymer at one site of the poly(alkylene oxide) moiety and terminated by substituents selected from, for example, H, OH, alkyl, alkoxy, or elements of a chelating agent as described above.

The cytotoxic agent can be a radioactive isotope, preferably a radioactive metal ion isotope such as represented by M in formula I above. The radioactive metal isotope can be an ion of an isotope of a metal selected, for example, from Sc, Fe, Pb, Ga, Y, Bi, Mn, Cu, Cr, Zn, Ge, Mo, Tc, Ru, In, Sn, Re, Sr, Sm, Lu, Du, Sb, W, Re, Po, Ta and Tl ions. Radioisotopes which are useful in diagnostic imaging applications which can be performed in conjunction with or are ancillary to the use of cytotoxic agents in the practice of this invention are specifically contemplated. Preferred isotopes of radioactive metal ions include $^{44}$Sc, $^{64,67}$Cu, $^{111}$In, $^{212}$Pb, $^{68}$Ga, $^{90}$Y, $^{153}$Sm, $^{212}$Bi, $^{99m}$Tc and $^{188}$Re for therapeutic and diagnostic imaging applications.

Other suitable cytotoxic agents include radionuclides, such as, for example, radioactive isotopes of I, In, Y, Sc, Ga, Ge, Tc and Re;

toxins such as diphtheria toxin A, abrin, ricin, modeccin, pokeweed antiviral protein, cobra venom factor, Pseudomonas exotoxin, gelonin, and other ribosome inactivating proteins, viscumin, and volkensin;

antibiotics, such as, for example, adriamycine, daunomycine, doctinomycin, daunorubican, doxorubicin, mithramycin, bleomycin, and mitomycin;

drugs, preferably selected from alkylating agents, antimetabolites, natural products, hormones and antagonists, and miscellaneous agents, such as radiosensitizers and complimentary oligonucleotide sequences.

Examples of alkylating agents include alkylating agents, having the bis-(2-chloroethyl)-amine group such as, for example, chlormethine, chlorambucile, melphalan, uramustine, mannomustine, extramustinephosphate, mechlore-thaminoxide, cyclophosphamide, ifosfamide, and trifosfamide;

alkylating agents having a substituted aziridine group such as, for example, tretamine, thiotepa, triaziquone and mitomycine;

alkylating agents of the alkyl sulfonate type, such as, for example, busulfan, piposulfan and piposulfam;

alkylating N-alkyl-N-nitrosourea derivatives, such as, for example, carmustine, lomustine, semustine, or streptozotocine; and alkylating agents of the mitobronitole, dacarbazine and procarbazine type.

Examples of antimetabolites include folic acid analogs, such as, for example, methotrexate;

pyrimidine analogs such as, for example, fluorouracil, floxuridine, tegafur, cytarabine, idoxuridine, and flucytosine; and, purine derivatives such as, for example, mercaptopurine, thioguanine, azathioprine, tiamiprine, vidarabine, pentostatin, and puromycine.

Examples of natural products include vinca alkaloids, such as, for example, vinblastine and vincristine;

epipodophylotoxins, such as, for example, etoposide and teniposide;

enzymes, such as, for example, L-asparaginase;

biological response modifiers, such as lymphokines and interferons, such as, for example, α-interferon, tumor necrosis factor, and interleukin 2;

camptothecin;

taxol;

prostaglandins, such as prostaglandin $E_2$; and, retinoids, such as retinoic acid.

Examples of hormones and antagonists include adrenocorticosteroids, such as, for example, prednisone;

progestins, such as, for example, hydroxyprogesterone caproate, medroxyprogesterone acetate and megestrol acetate;

estrogens, such as, for example, diethylstibestrol and ethinyl estradiol;

antiestrogens, such as, for example, tamoxifen;

androgens, such as, for example, testosterone propionate and fluoxymesterone;

antiandrogens, such as, for example, flutamide;

and gonadotropin-releasing hormone analogs, such as, for example, leuprolide.

Examples of miscellaneous agents include radiosensitizers, such as, for example, 1,2,4-benzotriazin-3-amine 1,4-dioxide and 1,2,4-benzotriazine-7-amine 1,4-dioxide;

platinum coordination complexes such as cisplatin and carboplatin;

anthracenedions, such as, for example, mitoxantrone;

substituted ureas, such as, for example, hydroxyurea;

and adrenocortical suppressants, such as, for example, mitotane and aminoglutethimide.

Examples of complimentary oligonucleotide sequences include antisense DNA sequences which are complimentary to and hybridize with segments of oncogenes so as to inhibit their activity.

In a preferred embodiment L and $L_1$ represent

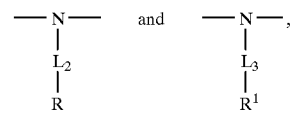

wherein $L_2$ and $L_3$ independently represent a chemical bond or a linking group such as described above, and R and $R^1$ independently represent H; or a substituent attached to the linking group such as described above.

The polymer of the invention can comprise both a therapeutic moiety and a moiety for enhancing contrast during x-ray or MR imaging.

For MR imaging applications, $M^{(+a)}$ preferably represents a paramagnetic metal ion such as an ion of metals of atomic number 21 to 29, 42, 44 and 57 to 71, especially 57 to 71. Ions of the following metals are preferred: Cr, V, Mn, Fe, Co, Ni, Cu, La, Ce, Pr, Nd, Pm, Sm, Eu, Gd, Tb, Dy, Ho, Er, Tm, Yb and Lu. Especially preferred are $Cr^{+3}$, $Cr^{+2}$, $V^{+2}$, $Mn^{+3}$, $Mn^{+2}$, $Fe^{+3}$, $Fe^{+2}$, $Co^{+2}$, $Gd^{+3}$ and $Dy^{+3}$. Alternatively, $M^{(+a)}$ can be $H^+$, in which case the polymer is in its nonmetallized acid form, or a metal ion such as $Li^+$, $Na^+$, $Al^{+3}$, $K^+$, $Ca^{+2}$, $Mg^{+2}$ $Cu^+$, $Cs^+$, $Zn^{+2}$ $Cu^{++}$, $Ag^+$ and $Sn^{++}$, or a basic nitrogen or phosphorus salt, such as a quaternary ammonium or phosphonium salt.

E can be one or more counterions. For example, E can be one or more anions, such as a halide, such as chloride and iodide; sulfate; phosphate; nitrate; and acetate. E can be one or more cations such as $Na^+$, $K^+$, meglumine, and the like. For in vivo applications, particularly for diagnostic imaging applications, nontoxic physiologically tolerable anions are, of course, desirable.

In structure I above, w is 0 or 1, r is 0 or 1, a is an integer preferably from 1 to 4, b is an integer preferably from 0 to 3, and d is an integer preferably from 0 to 4. When E is present, i.e., when w is 1, b most preferably is 1 or 2. d can range up to about 100 when Z comprises the residues of multiple chelating groups. The total positive charge on the cations equals the sum of the total charge on the residue of the chelating group plus the total charge on any counterions E present, i.e., a=d+b.

The metal content in the polymer of the invention can be 0, e.g., when $M^{(+a)}=H^+$, or it can vary from about 0.1 up to about 30% based on the total weight of the polymer. The metal can be present in an amount of 0.1–30%, preferably 1–25%, and more preferably 2–20% by weight.

The polymer in structure I can be capped at the termini with groups independently selected from Z, Q, L or $L_1$ to which is bound a terminal hydrogen atom, OH, alkyl, alkoxy, or elements of a linking group substituent such as described above. In preferred embodiments, wherein the polymer is a polyamide, the polymer can be capped with groups such as hydrogen or hydroxyl groups or with groups derived from polyamide chain terminating agents such as from monoamines and monoacyl derivatives such as monoanhydrides, e.g., acetic anhydride, or with groups derived from elements of the residue of a chelating group as defined above. It is further contemplated that cyclic polymers, i.e., non-capped polymers can be prepared.

The molecular weight (MW) of the polymer of this invention can vary widely, i.e., from about 1,000 to $10^8$ or greater, as measured by gel permeation chromatography (GPC). The polymer can be prepared in water-soluble, water-dispersible or water-insoluble forms, depending on the intended application. Water-soluble polymers generally are of MW from 1,000 to about 250,000. Water-insoluble crosslinked polymers generally are of MW from $10^5$ to $10^8$.

The polymer of this invention can be prepared by first contacting a reactive poly(alkylene oxide) species with a chelating agent or precursor thereof containing reactive functionality in a non-reactive solvent to form the polymer. The poly(alkylene oxide) species can be substituted or unsubstituted.

The preferred reaction conditions, e.g., temperature, pressure, solvent, etc., depend primarily on the particular reactants selected and can be readily determined by one skilled in the art.

Suitable reactive poly(alkylene oxide) species include terminally functionalized poly(alkylene oxide) diamines, poly(alkylene oxide) dihydrazines, poly(alkylene oxide) diisocyantes, poly(alkylene oxide) diols, poly(alkylene oxide) dialdehydes, poly(alkylene oxide) dicarboxylic acids, poly(alkylene oxide) bis(vinyl sulfonyl) ethers, poly(alkylene oxide) diphosphates, poly(alkylene oxide) N,N-dialkylaminophosphoramidates, poly(alkylene oxide) diepoxides, poly(alkylene oxide) dialkoxides, poly(alkylene oxide) disulfonates, poly(alkylene oxide) dihalides, and the like. The above-described poly(alkylene oxide) species are linear difunctional species. Tri- and higher multifunctional branched species relating to the above are also useful.

Suitable chelating agents and precursors thereof containing reactive functionality include polycarboxylic acids in dianhydride form, di(sulfonyl chlorides), di(alkyl sulfates), di(vinyl sulfones), diesters, and the like. As will be recognized by one skilled in the art, a suitably blocked progenitor to the chelating agent or precursor thereof containing reactive functionality can be contacted with the reactive poly(alkylene oxide) moiety to form the polymer, and then the blocking group can be subsequently removed by techniques known in the art. It is contemplated that additional chelating functional groups can be introduced by suitable chemical modification at the unblocked sites. If hydroxy substituents are to be selectively present in the final polymer, they preferably should be temporarily blocked during polymerization, e.g., by conventional blocking techniques, to minimize formation of undesirable byproducts, e.g., polyester- amide derived therefrom. However, for some purposes, polyester- polyamides which contain one or more ester linking groups in the backbone of the polymer are contemplated to be useful. The use of condensing agents such as carbodiimides is also contemplated to be useful in the formation of the polymers of this invention.

In a preferred embodiment, the polymer of this invention can be prepared by reacting a linear poly(alkylene oxide) diamine with a precursor of a chelating agent in an internal dianhydride form.

The poly(alkylene oxide) diamine can be prepared by reacting an activated form of the poly(alkylene oxide) with ammonia, a primary amine, a polyamine, an amide, or an azide followed by reduction. The amino group can be introduced by other methods known in the art. Suitable illustrative amines include N-methylamine, amino acids, aminomethyl pyridine, aminomethylthiophene, methoxyethoxyethylamine, methoxyethylamine and aminobenzoic acid. Exemplary useful polyamines include diaminohexane, tris(aminoethyl)amine, and diethylenetriamine.

The linear poly(alkylene oxide) in its diol form is widely available commercially or can be prepared by techniques well known to those skilled in the art. The poly(alkylene oxide) is activated for nucleophilic displacement by reacting it with an activator such as p-toluenesulfonyl chloride, thionyl chloride, thionyl bromide, an alkylsulfonyl chloride, e.g., $CH_3SO_2Cl$, a sulfonic acid anhydride, or any other suitable activator known in the art. The activated form of the poly(alkylene oxide) thus can be a ditosylate, a dichloride, a dibromide, etc.

The activated form of the poly(alkylene oxide) is reacted preferably with a stoichiometric excess of the amine, in an inert solvent preferably at a temperature, e.g., 100–160° C., and pressure, e.g., 1 to 10 atmospheres, sufficient to drive the reaction to completion. Suitable solvents include dioxane, ethanol, and other alcohols. Thereafter, the poly(alkylene oxide) diamine preferably is isolated, e.g., by evaporation or precipitation, and purified, e.g., by dissolving in a suitable solvent such as methylene chloride, chloroform or trichloroethane, and then washing the solution with an excess of aqueous NaOH, or by any other suitable isolation and purification techniques.

The internal anhydride forms of the chelating agents described above are commercially available and/or can be prepared by techniques known in the art. For example, the internal anhydride forms of EDTA and DTPA are commercially available. The internal anhydride forms of DOTA, DO3A, OTTA, B4A, P4A and TMT can be prepared by techniques known in the art. For example, the anhydrides can-be prepared by heating the corresponding acids in acetic anhydride in the presence of pyridine as catalyst. Methods for the preparation of B4A, P4A and TMT are described in U.S. Pat. No. 4,859,777. Mixed anhydrides are also suitable.

The reactive poly(alkylene oxide) diamine can be reacted with the internal dianhydride in a non-reactive solvent to form the unmetallized polymer. The reaction conveniently can take place at approximately room temperature and atmospheric pressure. However, higher and lower temperatures and pressures are contemplated. Suitable solvents include dimethylsulfoxide, dimethylformamide, acetonitrile, chloroform, dichloromethane and 1,2-dichloroethane. The nonmetallized polymer preferably is isolated and then purified, e.g., by diafiltration.

Cytotoxic agents that are covalently linked to the polymer can be covalently attached to elements of the chelating group or to elements of the linking group by chemical bonds or by linking groups as described above. Covalent bond formation can be accomplished by methods well known in the art, such as, for example, ester and amide formation using carbodiimide condensing agents.

In a preferred embodiment, the metallized polymer can be formed by contacting the unmetallized polymer sequentially or simultaneously with one or more sources of metal ions. This can be conveniently accomplished by adding one or more metal ion solutions or one or more metal ion solid salts or metal ion oxides, preferably sequentially, to a solution, preferably an aqueous solution, of the polymer. Thereafter, or between sequential addition of metal ions, the chelated polymer preferably is diafiltered in water to remove excess unbound metal.

A general reaction scheme for this method of preparing the polymers of this invention and illustrative examples are set forth below.

Alternatively, the polymer can be prepared in a condensation polymerization reaction between a suitable diamine and a diacid containing the metallized chelating group or a covalently attached cytotoxic agent suitably protected from reaction with the amine, in a suitably activated form, e.g., in the form of an activated diester. In the case of a covalently attached cytotoxic agent, the agent can be suitably deblocked after polymer formation.

The molecular weight of the polymer product depends upon many factors including, for example, the molecular weight of the starting poly(alkylene oxide) moiety, the presence or absence of reactive polymerization chain terminating agents (such as monoanhydrides or monoamines in the case of polyamides) which reduce molecular weight by end-capping the polymer during the polymerization process, the absence or presence of reactive crosslinkers or low molecular weight chain extenders which increase the MW of the polymer during polymerization, and the relative concentrations of the poly(alkylene oxide) and chelator moiety present during the polymerization reaction which in turn affects the number of recurring units in the polymer product. To form the polymer of this invention in a water-insoluble form, the above described procedure can be modified to incorporate a crosslinker, e.g., a crosslinkable tri- or higher polyamine, and/or by adding a reactive crosslinking agent, which can be the reactive chelating moiety, or , e.g., a diacid or higher acid chloride, to the polymerization reaction. The preparation of insoluble and water-soluble polymers of molecular weight 1,000 to $10^8$ can be accomplished by routine experimentation by one skilled in the art of polymer synthesis techniques.

In some embodiments, the above-described polymer can contain an immunoreactive group covalently bonded thereto through a protein reactive group. As used herein, the term "immunoreactive group" is meant to include an organic compound which is capable of covalently bonding to the polymer and which is found in a living organism or is useful in the diagnosis, treatment or genetic engineering of cellular material or living organisms, and which has a capacity for interaction with another component which may be found in biological fluids or associated with cells to be treated such as tumor cells.

Depending upon the intended use, the immunoreactive group can be selected from a wide variety of naturally occurring or synthetically prepared materials, including, but not limited to enzymes, amino acids, peptides, polypeptides, proteins, lipoproteins, glycoproteins, hormones, drugs (for example digoxin, phenytoin, phenobarbitol, thyrozine, triiodothyronine, gentamicin, carbamazepine, and theophylline), steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies, antigenic materials (including proteins and carbohydrates), avidin and derivatives thereof, biotin and derivatives thereof, and others known to one skilled in the art.

Preferred immunoreactive groups are those which have a receptor molecule specific to a ligand of interest. Thus, a specific binding reaction involving the reagent can be used for the targeting expected. Examples of such ligand-receptor complexes include, but are not limited to antibody-antigen, avidin-biotin, repressor (inducer)—promoter of operons and sugar-lectin complexes. Additionally, complementary nucleic acids, i.e., a hybridized product of complementary strands, are also considered specific binding materials as the term is used herein.

Useful immunoreactive groups include (1) any substance which, when presented to an immunocompetent host, will result in the production of a specific antibody capable of binding with that substance, or (2) the antibody so produced, which participates in an antigen-antibody reaction. Thus, the immunoreactive group can be an antigenic material, an antibody, or an anti-antibody. Both monoclonal and polyclonal antibodies are useful. The antibodies can be whole molecules or various fragments thereof, as long as they contain at least one reactive site for reaction with the reactive groups on the complexing agent or with linking groups as described herein.

In certain embodiments, the immunoreactive group can be an enzyme which has a reactive group for attachment to the complexing agent. Representative enzymes include, but are not limited to, aspartate aminotransaminase, alanine aminotransaminase, lactate dehydrogenase, creatine phosphokinase, gamma glutamyl transferase, alkaline acid phosphatase, prostatic acid phosphatase, horseradish peroxidase and various esterases.

If desired, the immunoreactive group can be modified or chemically altered to provide reactive groups for attaching to the polymer by techniques known to those skilled in the art. Such techniques include the use of linking moieties and chemical modification such as described in WO-A-89/02931 and WO-A-89/2932, which are directed to modification of oligonucleotides, and U.S. Pat. No. 4,719,182.

Two highly preferred uses for the compositions of this invention are for the diagnostic imaging of tumors and the radiological treatment of tumors. Preferred immunological groups therefore include antibodies, or immunoreactive fragments thereof, to tumor-associated antigens. Specific examples include B72.3 antibodies (described in U.S. Pat. Nos. 4,522,918 and 4,612,282) which recognize colorectal tumors, 9.2.27 anti-melanoma antibodies, D612 antibodies which recognize colorectal tumors, UJ13A antibodies which recognize small cell lung carcinomas, NRLU-10 antibodies which recognize small cell lung carcinomas and colorectal tumors (Pan-carcinoma), 7E11C5 antibodies which recognize prostate tumors, CC49 antibodies which recognize colorectal tumors, TNT antibodies which recognize necrotic tissue, PR1A3 antibodies, which recognize colon carcinoma, ING-1 antibodies, which are described in International Patent Publication WO-A-90/02569, B174 antibodies which recognize squamous cell carcinomas, B43 antibodies which are reactive with certain lymphomas and leukemias and others which may be of particular interest.

Such antibodies and other useful immunological groups described above are large, complex molecules having multiple sites for appendage of the complexing agent. Consequently, the immunoreactive group can have appended to it additional complexing agents via one of the protein reactive groups. Thus, the term immunoreactive group is intended to include immunological groups having polymer molecules bonded thereto through one or more protein reactive groups.

Additionally, an antibody or fragment thereof containing a carbohydrate region can be attached to the polymer through the carbohydrate region of the antibody, such as described in U.S. Pat. No. 4,937,183. Useful methods for attaching an antibody are also described in U.S. Pat. Nos. 4,671,958; 4,699,784; 4,741,900; and 4,867,973.

By "protein reactive group" it is meant any group which can react with any functional groups typically found on proteins. However, it is specifically contemplated that the protein reactive group can be conjugated to nonprotein biomolecules and to cytotoxic agents. Thus the protein reactive groups useful in the practice of this invention include those groups which can react with any biological molecule containing an immunoreactive group, whether or not the biological molecule is a protein to form a linking group between the complexing agent and the immunoreactive group.

Preferred protein reactive groups can be selected from but are not limited to: (1) A group that will react directly with the amine or sulfhydryl groups on the protein or biological molecule containing the immunoreactive group, for example, active halogen containing groups including, for example, chloromethylphenyl groups and chloroacetyl [Cl—CH$_2$CO—] groups, activated 2-leaving group substituted ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents. (2) A group that can react readily with modified proteins or biological molecules containing the immunoreactive group, i.e., proteins or biological molecules containing the immunoreactive group modified to contain reactive groups such as those mentioned in (1) above, for example, by oxidation of the protein to an aldehyde or a carboxylic acid, in which case the "protein reactive group" can be selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 18 carbon atoms as described for R above. The aryl portions of the protein reactive group can contain from about 6 to about 20 carbon atoms as described for R above. (3) A group that can be linked to the protein or biological molecule containing the immunoreactive group, or to the modified protein as noted in (1) and (2) above by use of a crosslinking agent. Certain useful crosslinking agents, such as, for example, difunctional gelatin hardeners, bisepoxides and bisisocyanates become a part of, i.e., a linking group in, the protein-complexing agent conjugate during the crosslinking reaction. Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847 and the dication ethers of U.S. Pat. No. 4,877,724. With these crosslinking agents, one of the reactants must have a carboxyl group and the other an amine, alcohol, or sulfhydryl group. The crosslinking agent first reacts selectively with the carboxyl group, then is split out during reaction of the "activated" carboxyl group with, for example, an amine to form an amide linkage between the protein or cytotoxic agent and metal complexing agents, this covalently bonding the two moieties. An advantage of this approach is that crosslinking of like molecules, e.g., proteins with proteins or complexing agents with complexing agents is avoided, whereas the reaction of difunctional crosslinking agents is less selective and unwanted crosslinked molecules can be obtained. Especially preferred protein reactive groups include amino and isothiocyanato. It is contemplated that the above methods can be applied to the covalent attachment of cytotoxic agents, suitably protected and subsequently deprotected and activated by methods well known in the art.

The present invention includes one or more of the polymers of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders and lyophilizates for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, cryoprotecting, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated as being within the scope of this invention.

Actual dosage levels of active ingredient in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided dose may be in amounts, for example, of from about 1 picomol to about 10 millimol of cytotoxic agent per kilogram of body weight. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The following examples further illustrate the invention and are not be be construed as limiting of the specification and claims in any way.

EXAMPLE 1

A composition of the invention (Ia) was prepared in accordance with the reaction scheme described below.

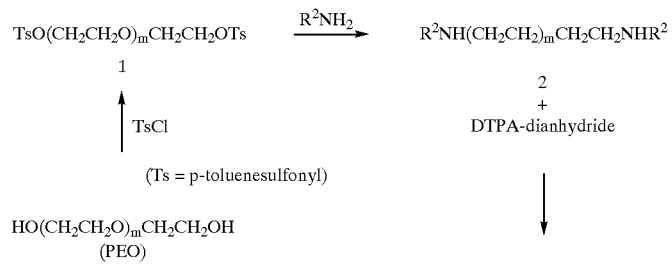

-continued

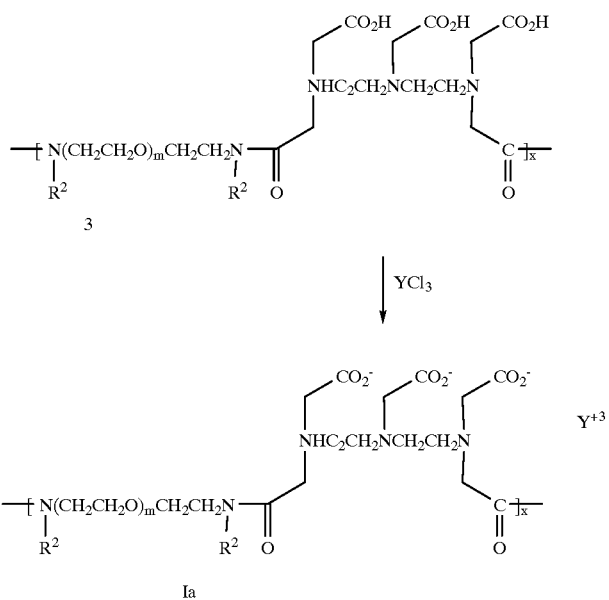

A solution of 100.0 g (0.0690 mol) of PEO of average molecular weight (MW) 3350 in toluene (1500 ml) was refluxed for 2 hours with azeotropic removal of water. The solution was cooled to 25° C. and then treated with triethylamine (46.1 ml, 0.331 mol), 4-dimethylaminopyridine (1.69 g, 0.0138 mol) and p-toluenesulfonyl chloride (57.9 g, 0.303 mol) and heated for 4 days at 60° C. under an atmosphere of nitrogen. After cooling to room temperature, the reaction mixture was filtered and the filtrate was extracted twice with water. The combined aqueous extracts were washed with ether, then extracted twice with $CHCl_3$. The $CHCl_3$ extracts were dried over anhydrous magnesium sulfate and concentrated to yield 121.3 g of product (1).

A solution of 42.2 g (0.0240 mol) of the bis-tosylate 1 in 420 ml of dioxane was cooled in an ice bath and a stream of methylamine was introduced over a period of 35 minutes. The reaction mixture was then heated in a stainless steel reactor at 160° C. for 16 hours, then cooled to room temperature and filtered. The filtrate was concentrated to remove solvent, then treated with water (844 ml) and 1.0N NaOH (95.2 ml) and extracted twice with $CHCl_3$. The $CHCl_3$ extracts were dried over anhydrous magnesium sulfate and concentrated to leave 31.0 g of product (2) ($R^2$=$CH_3$).

A solution of 9.00 g (6.10 mmol) of the bis-(N-methylamine) 2 in 45 ml of dimethylsulfoxide (DMSO) was treated with triethylamine (1.70 ml, 12.2 mmol) and a solution of 2.18 g (6.10 mmol) of diethylenetriaminepentaacetic acid dianhydride in DMSO (45 ml). The reaction mixture was stirred at room temperature for 16 hours, then treated with 360 mls of water. The resultant solution was filtered through a 0.45 μm nylon filter and the filtrate diafiltered against water in a diafiltration cell equipped with a 3000 MW cut-off membrane leaving 170 mls of a solution of (3) ($R^2$=$CH_3$).

Polymeric yttrium-90 chelate was prepared by the addition of 1 μCi $^{90}YCl_3$ per μg of polymer followed by a 10-fold excess of non-radioactive $YCl_3.6H_2O$. The radiolabeled polymer was purified using a PD-10 (Pharmacia LKB Biotechnology) desalting column. The polymeric yttrium-90 chelate was determined to have an average MW of 28,900 (as determined by SEC-HPLC using PEO molecular weight standards).

A PBS solution of the radiolabeled chelate was injected into the tail vein of HT29 tumor bearing nude mice at a dose of 16 μCi per mouse. Animals were sacrificed at 1, 4 and 24 hours; tumors were removed, weighed and counted:

| Time | % Injected Dose |
| --- | --- |
| 1 | 1.6 |
| 4 | 2.0 |
| 24 | 2.2 |

EXAMPLE 2

Example 1 was repeated except that the starting PEO had an average MW of 1,000. The product was determined to have an average MW of 13,100.

EXAMPLES 3–5

Example 1 was repeated three times except that the starting PEO had an average MW of 1,500. The products were determined to have an average MW of 13,500, 14,300 and 18,600.

EXAMPLE 6

Example 1 was repeated except that the starting PEO had an average MW of 1,500 and $R^2$=H. The product was determined to have an average MW of 23,700.

EXAMPLE 7

In a manner similar to Example 1, a polymeric gadolinium chelate of MW 16,300 containing radioactive $^{153}Gd$ was prepared from PEO of MW 1450. This product was employed in biodistribution studies in rats to determine a blood-pool half-life (elimination phase) of 75 minutes.

EXAMPLE 8

In a manner similar to Example 1, a polymeric gadolinium chelate of MW 8,010 containing radioactive $^{153}$Gd was prepared from PEO of MW 1000. This product was employed in biodistribution studies in rats to determine a blood-pool half-life (elimination phase) of 48 minutes.

EXAMPLE 9

In a manner similar to Example 1, a polymeric gadolinium chelate of MW 22,800 containing radioactive $^{153}$Gd was prepared from PEO of MW 2000. This product was employed in biodistribution studies in rats to determine a blood-pool half-life (elimination phase) of 74 minutes.

EXAMPLE 10

In a manner similar to Example 1, a polymeric gadolinium chelate of MW 22,400 containing radioactive $^{153}$Gd was prepared from PEO of MW 3350. This product was employed in biodistribution studies in rats to determine a blood-pool half-life (elimination phase) of 141 minutes.

The invention has been described in detail with particular reference to certain preferred embodiments thereof, but it will be understood that variations and modifications can be effected within the spirit and scope of the invention.

What is claimed:

1. A polymer of molecular weight $10^3$ to $10^8$ comprising a plurality of polymer repeat units, said units providing in the polymer backbone a poly(alkylene oxide) moiety of molecular weight 250 to 20,000 linked to a chelant moiety selected from the group consisting of B4A, P4A, PheMT and TMT, and having a cytotoxic agent associated therewith.

2. The polymer of claim 1 wherein one or more chelant moiety has a radionuclide associated therewith.

3. The polymer of claim 1 wherein said polymer comprises from 2 to 1000 of said units.

4. The polymer of claims 1 wherein said units have the structure

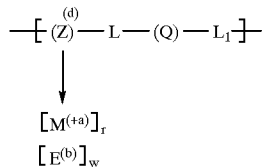

wherein:
Z is the chelant moiety;
Q is a poly(alkylene oxide) moiety;
$M^{(+a)}$ is one or more radioactive metal ions having a total charge of +a;
L and $L_1$ independently represent a chemical bond or a linking group;
$E^{(b)}$ is one or more counterions having a total charge of b;
w is 0 or 1;
r is 0 or 1;
d is the total charge on the linked residue of the chelating group; and
a=d+b.

5. The polymer of claim 4 wherein Q is selected from the group consisting of a poly(ethylene oxide) moiety, a poly(propylene oxide) moiety and a poly(ethylene oxide)-co-poly(propylene oxide) moiety of MW 250–10,000.

6. The polymer of claim 4 wherein L and $L_1$ independently represent amino, imido, nitrilo, imino, alkylene, carbonyl, sulfonyl, sulfinyl, ether, thioether, ester, thioester, amide, thioamide, thio, dithio, phosphate, phosphonate, urelene, thiourelene, urethane, thiourethane, an amino acid linkage or a peptide linkage.

7. The polymer of claim 4 wherein L and $L_1$ independently represent

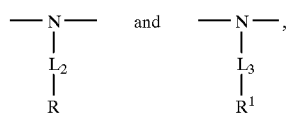

$L_2$ and $L_3$ independently represent a chemical bond or a linking group; and R and $R^1$ independently represent H, OH, alkyl, aryl, halogenated aryl, aralkyl, alkoxy, heterocyclyl, a carboxyl group, an ester group, the chelant moiety or a poly(alkylene oxide) moiety.

8. The polymer of claim 1 wherein said units are recurring units having the structure

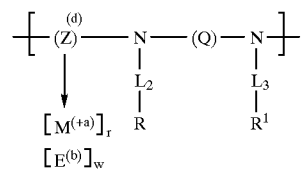

wherein:
Z is the chelant moiety;
Q is a poly(alkylene oxide) moiety,
$M^{(+a)}$ is one or more radioactive metal ions having a total charge of +a;
$L_2$ and $L_3$ independently represent a chemical bond or a linking group;
R and $R^1$ independently are H, OH, alkyl, aryl, halogenated aryl, aralkyl, halogenated aralkyl, alkoxy, heterocyclyl, a carboxyl group, a carboxylate group, an ester group, the chelant moiety or a poly(alkylene oxide) moiety;
$E^{(b)}$ is one or more counterions having a total charge of b;
w is 0 or 1;
r is 0 or 1;
d is the total charge on the residue of the chelating group, and
a=d+b.

9. The polymer of claim 8 wherein, $M^{(+a)}$ is $Y^{+3}$ or $In^{+3}$, r is 1, w is 0, $L_2$ and $L_3$ represent a chemical bond, Q is a poly(ethylene oxide) moiety of MW 250–10,000, and R and $R^1$ are H or $CH_3$.

10. A pharmaceutical composition comprising the polymer of claim 1 and a pharmaceutically acceptable carrier.

11. A method of diagnostic imaging a site in a body comprising a) administering to the body a contrast enhancing amount of the polymer of claim 2, capable of targeting the site, and b) imagewise activating a radiation sensitive element or device with the radiation emitted from said site.

12. A method for treating disease sites in a patient comprising administering to the patient or a specimen from the patient an effective amount of the polymer of claim 1.

13. The polymer of claim 1 wherein one or more chelating agents therein has a paramagnetic metal ion associated therewith.

14. A method of diagnostic imaging a site in a body comprising a) administering to the body a contrast enhancing amount of the polymer of claim 13 capable of targeting the site, and b) then exposing said body to a magnetic resonance measurement step to derive an image of at least a portion of the targeted site.

15. The polymer according to claim 1 wherein the cytotoxic agent comprises a radioactive isotope of Y, In or Tc.

* * * * *